US012751985B2

(12) United States Patent
Fine

(10) Patent No.: US 12,751,985 B2

(45) Date of Patent: Oct. 6, 2026

(54) ORAL AND INTESTINAL HEALTH PRODUCTS

(71) Applicant: Kenneth Davin Fine, Dallas, TX (US)

(72) Inventor: Kenneth Davin Fine, Dallas, TX (US)

( * ) Notice: Subject to any disclaimer, the term of this patent is extended or adjusted under 35 U.S.C. 154(b) by 679 days.

(21) Appl. No.: 16/126,858

(22) Filed: Sep. 10, 2018

(65) Prior Publication Data

US 2019/0076497 A1 Mar. 14, 2019

Related U.S. Application Data

(60) Provisional application No. 62/556,682, filed on Sep. 11, 2017.

(51) Int. Cl.

| | |
|---|---|
| ***A61K 36/45*** | (2006.01) |
| ***A23L 2/02*** | (2006.01) |
| ***A23L 2/60*** | (2006.01) |
| ***A23L 33/135*** | (2016.01) |
| ***A23L 33/16*** | (2016.01) |
| ***A61K 8/02*** | (2006.01) |
| ***A61K 8/19*** | (2006.01) |
| ***A61K 8/23*** | (2006.01) |
| ***A61K 8/368*** | (2006.01) |
| ***A61K 8/58*** | (2006.01) |
| ***A61K 8/9789*** | (2017.01) |
| ***A61K 8/99*** | (2017.01) |
| ***A61K 9/00*** | (2006.01) |
| ***A61K 9/14*** | (2006.01) |
| ***A61K 31/29*** | (2006.01) |
| ***A61K 33/04*** | (2006.01) |
| ***A61K 33/14*** | (2006.01) |
| ***A61K 35/741*** | (2015.01) |
| ***A61K 35/742*** | (2015.01) |
| ***A61K 35/744*** | (2015.01) |
| ***A61K 35/745*** | (2015.01) |
| ***A61K 35/747*** | (2015.01) |
| ***A61K 36/82*** | (2006.01) |
| ***A61K 36/87*** | (2006.01) |
| ***A61P 1/00*** | (2006.01) |
| ***A61P 1/02*** | (2006.01) |
| ***A61P 1/14*** | (2006.01) |
| ***A61Q 11/00*** | (2006.01) |
| *A61K 35/00* | (2006.01) |

(52) U.S. Cl.

CPC ................ *A61K 36/45* (2013.01); *A23L 2/02* (2013.01); *A23L 2/60* (2013.01); *A23L 33/135* (2016.08); *A23L 33/16* (2016.08); *A61K 8/022* (2013.01); *A61K 8/027* (2013.01); *A61K 8/19* (2013.01); *A61K 8/23* (2013.01); *A61K 8/368* (2013.01); *A61K 8/58* (2013.01); *A61K 8/9789* (2017.08); *A61K 8/99* (2013.01); *A61K 9/0053* (2013.01); *A61K 9/0095* (2013.01); *A61K 9/14* (2013.01); *A61K 31/29* (2013.01); *A61K 33/04* (2013.01); *A61K 33/14* (2013.01); *A61K 35/741* (2013.01); *A61K 35/742* (2013.01); *A61K 35/744* (2013.01); *A61K 35/745* (2013.01); *A61K 35/747* (2013.01); *A61K 36/82* (2013.01); *A61K 36/87* (2013.01); *A61P 1/00* (2018.01); *A61P 1/02* (2018.01); *A61P 1/14* (2018.01); *A61Q 11/00* (2013.01); *A23V 2400/113* (2023.08); *A23V 2400/169* (2023.08); *A23V 2400/175* (2023.08); *A23V 2400/181* (2023.08); *A23V 2400/517* (2023.08); *A23V 2400/533* (2023.08); *A61K 2035/115* (2013.01); *A61K 2800/412* (2013.01); *A61K 2800/58* (2013.01)

(58) Field of Classification Search

CPC ...................................................... A61K 36/45

See application file for complete search history.

(56) References Cited

U.S. PATENT DOCUMENTS

| | | | | |
|---|---|---|---|---|
| 2003/0082277 A1* | 5/2003 | Sokhey | A23P 20/15 426/92 |
| 2006/0018843 A1* | 1/2006 | Fine | A61K 8/9728 424/48 |
| 2010/0330197 A1* | 12/2010 | Higashiguchi | A61P 43/00 424/638 |
| 2012/0076914 A1* | 3/2012 | Langford | A23L 29/294 426/601 |
| 2014/0044809 A1* | 2/2014 | Brainard | A61K 31/194 424/732 |

(Continued)

FOREIGN PATENT DOCUMENTS

| | | | |
|---|---|---|---|
| JP | 2017088580 A * | 5/2017 | A61K 8/99 |
| WO | WO-2007000648 A1 * | 1/2007 | A61K 31/519 |

OTHER PUBLICATIONS

Epsom Salt, dailymed.nlm.nih.gov, revised on Nov. 2017, printed from https://dailymed.nlm.nih.gov/dailymed/fda/fdaDrugXsl.cfm?setid=8d0b341f-81b4-49a0-a712-1e0c79f778fc&type=display on May 21, 2021. (Year: 2017).*

(Continued)

*Primary Examiner* — Gina C Justice

(74) *Attorney, Agent, or Firm* — Ferguson Braswell Fraser Kubasta PC

(57) ABSTRACT

In various implementations, one or more compositions may be provided to improve or maintain oral and/or intestinal health. For example, a dental powder, toothpaste, mouthwash, and/or probiotic composition may be administered to improve or maintain oral and/or intestinal health. In some implementations, an intestinal health kit that includes cleanse compositions, renewal compositions, and/or digestion aids (e.g., enzymes) may be administered to improve or maintain intestinal health and/or fitness.

16 Claims, 1 Drawing Sheet

(56) References Cited

U.S. PATENT DOCUMENTS

| | | | | |
|---|---|---|---|---|
| 2014/0161878 | A1* | 6/2014 | Ockerman | A61K 31/51 424/451 |
| 2016/0008392 | A1* | 1/2016 | Taniguchi | A61K 31/718 514/60 |
| 2016/0166501 | A1* | 6/2016 | Yudina | A61K 35/747 424/50 |
| 2016/0287644 | A1* | 10/2016 | Rahm | A61K 35/20 |
| 2016/0324765 | A1* | 11/2016 | Fine | A61K 8/99 |
| 2017/0056459 | A1* | 3/2017 | Keegan | A61K 31/375 |

OTHER PUBLICATIONS

Koo et al., "Pharmacological Effects of Green Tea on the Gastrointestinal System," European Journal of Pharmacology, 2004, 500: 177-184. (Year: 2004).*

Lusinski, N., "11 Surprising uses for Epsom salt in and around your house", Feb. 11, 2016, www.simplemost.com, printed from https://www.simplemost.com/surprising-uses-for-epsom-salt-in-and-around-your-home/ on Mar. 19, 2022. (Year: 2016).*

Natural Epsom Salt, "Amoray Care", Product Description, Revised on Oct. 2014. (Year: 2014).*

"Lactobacillus GG: A potent immune regulator effective in many disorders", Oct. 7, 2009, www.clinicaleducation.org, printed from https://www.clinicaleducation.org/resources/reviews/lactobacillus-gg-a-potent-immune-regulator-effective-in-many-disorders/ on Mar. 19, 2022. (Year: 2009).*

* cited by examiner

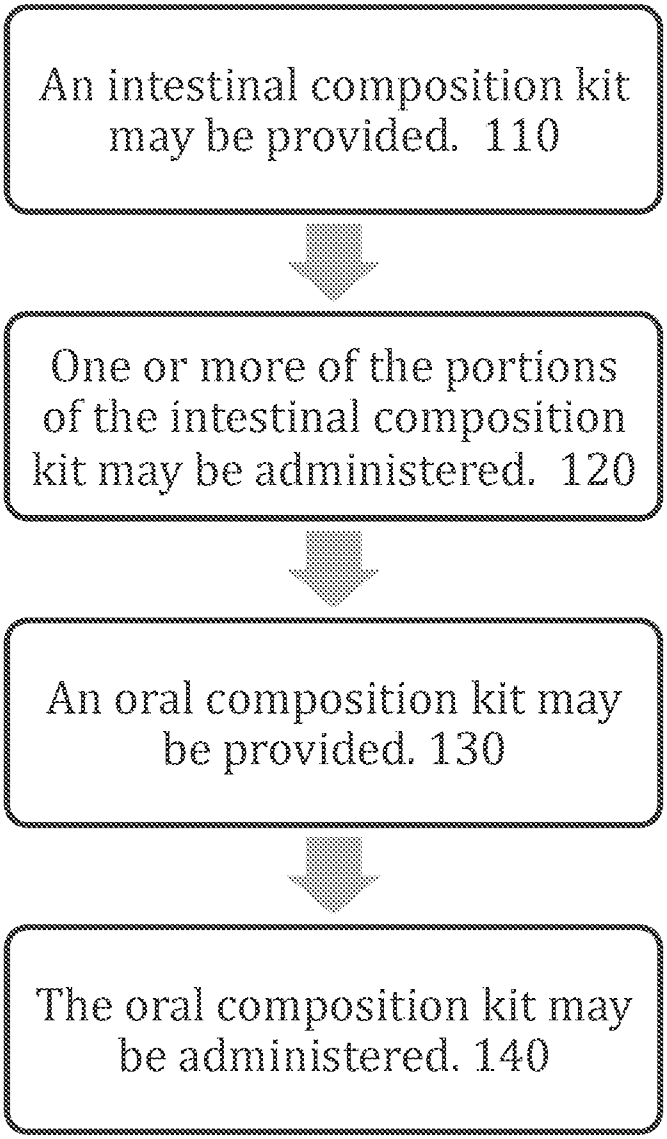
An intestinal composition kit may be provided. 110
One or more of the portions of the intestinal composition kit may be administered. 120
An oral composition kit may be provided. 130
The oral composition kit may be administered. 140

ORAL AND INTESTINAL HEALTH PRODUCTS

CROSS-REFERENCE TO RELATED APPLICATION

This application claims the benefit of U.S. Provisional Application No. 62/556,682 filed Sep. 11, 2017 and entitled "ORAL AND INTESTINAL HEALTH PRODUCTS", which is incorporated by reference for all purposes herein.

TECHNICAL

The present invention relates to products that improve or maintain intestinal and/or oral health.

BACKGROUND

Intestinal cleanses are commonly performed prior to medical and surgical procedures involving the colon and/or abdomen, after illnesses, and/or to promote general health. For example, harsh chemicals such as polyethylene glycol-electrolyte lavage solution (PEG-ELS) and sodium phosphate solutions are commonly used to cleanse the bowel prior to colonoscopies. However, these harsh solutions can cause abdominal pain and distension, can be difficult for patients to ingest (e.g., since they have a repulsive taste and involve ingestion of large volumes of fluid to ingest, such as with PEG-ELS), and can cause complications related to their chemical properties. Common fruit juice, psyllium-seed, and/or herb cleanses often have minimal efficacy when employed for cleansing the bowl and/or intestines.

SUMMARY

In various implementations, gastrointestinal health may be promoted by the application of oral and/or intestinal compositions. The oral compositions may include dental powder, toothpaste, mouthwash, and/or oral probiotic compositions. The dental powder may include an antacid, an anti-cavity probiotic, and a special blueberry fiber. The toothpaste and/or mouthwash may include minerals, essential oils, medicinal herbs (e.g., based on Western herbs and/or Chinese herbs), and/or bismuth subsalicylate. Administration of one or more of the oral compositions may promote growth of healthy oral flora, improve mouth health (e.g., reduce inflammation, inhibit (e.g., prevent) and/or treat gingivitis, inhibit (e.g., prevent) and/or treat periodontitis, etc.), and/or improve intestinal health and/or fitness.

In various implementations, the intestinal compositions may include a cleanse composition, an intestinal flora renewal composition, and/or an intestinal maintenance composition. An intestinal composition may be administered separately and/or in conjunction with other intestinal compositions. The cleanse composition may include hydrate of magnesium sulfate. The cleanse composition may include juice and/or a sweetener, in some implementations. Administration of one or more dosages of the cleanse composition may cleanse the intestinal tract (e.g., bowels) for pre-medical procedure preparation, after illness, and/or to improve intestinal and/or overall health. The renew composition may include probiotics and/or fiber, such as a special fiber derived from blueberries. The renew composition may be administered after the cleanse composition, in some implementations. The intestinal maintenance composition may include probiotics, fiber (e.g., the special fiber derived from blueberries), and/or digestive enzymes administered during the ingestion of meals.

In some implementations, a kit may be provided for generating at least a portion of the probiotics. For example, probiotics generated from the kit may be utilized to replace, allow a user to create, and/or supplement at least a portion of the renew and/or intestinal maintenance compositions. The kit may include an initial culture that is allowed to grow (e.g., reproduce) in a substance, such as a fiber and/or juice.

In various implementations, one or more compositions may be orally administered to improve and/or maintain gastrointestinal health of an individual. One or more cleanse compositions and one or more renew compositions may be administered orally. A cleanse compositions may include magnesium sulfate and/or fruit juice. The fruit juice may include blueberry juice. A renew compositions may include fiber and/or probiotic. Administration of the renew composition(s) after the administration of cleanse composition(s) may improve or maintain gastrointestinal health of an individual.

Implementations may include one or more of the following features. The renew compositions may not include fiber, in some implementations. A cleanse composition may include green tea. The cleanse composition may include grape juice and/or sweetener. The sweetener may be a sugar substitute. A cleanse compositions may include approximately 3/16 to approximately 1/4 teaspoon of sweetener. The cleanse compositions may include approximately 20 to approximately 40 cc of Magnesium sulfate. A cleanse compositions may include approximately 20 to approximately 40 cc of Magnesium sulfate, approximately 4 to approximately 5 ounces of the fruit juice, and/or approximately 3/16 to approximately 1/4 teaspoon of sweetener. The fiber of the renew composition may include blueberry fiber, and wherein blueberry fiber comprises remnants of blueberries after blueberry juicing. The probiotic of the renew composition may include at least one high efficacy strain and at least one other bacteria strain. In some implementations, the renew composition may include at least one high efficacy strain and a plurality of other bacteria strains. The other bacteria strains of the probiotic may include *Lactobacillus acidophilus; Lactobacillus plantarum, Lactobacillus rhamnosus, bifidobacterium bifidus, Lactobacillus salivarius, Bificobacterium bifandus, Bifidobacterium lactis*, and *Bifidobacterium longum*. The cleanse composition and/or the renew composition may be administered in more than one dosage. In some implementations, a second cleanse composition may be orally administered after a first predetermined period of time (e.g., greater than approximately 3 hours) after the first cleanse composition is orally administered. A second renew composition may be orally administered after a second period of time (e.g., greater than approximately 6 hours) after the administration of the first renew composition.

In various implementations, one or more compositions may be orally administered to improve and/or maintain gastrointestinal health of an individual. One or more oral probiotic composition and one or more renew compositions may be orally administered. An oral probiotic may include at least one first bacteria associated with oral health and at least one second bacteria associated with gastrointestinal health. The probiotic composition may be administered via an immediate delivery vehicle. The renew composition(s) may include at least 30 billion of one or more third bacteria (e.g., measured at manufacture and/or measured prior to consumption). The third bacteria may include a high efficacy strain of bacteria. The renew composition may include one or more fourth bacteria associated with lower gastrointestinal health. The renew composition may be administered via a delivery vehicle that inhibits release in the stomach of the individual. The administration of probiotic compositions with the administration of the cleanse compositions may improve and/or maintain lower gastrointestinal health of an individual.

Implementations may include one or more of the following features. Additional dosages of the oral probiotic composition and/or the renew composition may be orally administered (e.g., after a period of time such as greater than approximately 6 hours after the previous administration). The oral probiotic composition and/or the renew composition may be administered in more than one dose. For example, the high efficacy strain may be administered in a first capsule(s) and the other bacteria may be administered in second capsule(s) for administration of the renew composition. In some implementations, at least one first bacteria associated with oral health may include *Streptococcus salivarius* BLIS K12. At least one second bacteria associated with gastrointestinal health in the oral probiotic composition may include *Lactobacillus rhamnosus, Lactobacillus paracasei, Lactobacillus plantation, Lactobacillus reuteri*, and/or *Lactobacillus salivarius*. The third bacteria may include *Lactobacillus* GG and/or at least one of the fourth bacteria associated with lower gastrointestinal health may include *Lactobacillus acidophilus, Lactobacillus plantation, Lactobacillus rhamnosus, Bifidobacterium bifidus, Lactobacillus salivarius, Bificobacterium bifandus, Bifidobacterium lactis*, and/or *Bifidobacterium longum*. In some implementations, a dental powder and/or a mouthwash may be administered prior to orally administering the oral probiotic composition. In some implementations, the oral probiotic composition may be delivered as a mouthwash. The administration of the oral probiotic may or may not include swallowing the oral probiotic.

In various implementations, one or more compositions may be orally administered to improve and/or maintain gastrointestinal health of an individual. A dental powder and/or a mouthwash may be orally administered prior to orally administering the oral probiotic composition. The oral probiotic composition may be administered. The oral probiotic may include at least one first bacteria associated with oral health and at least one second bacteria associated with gastrointestinal health. The probiotic composition may be administered via an immediate delivery vehicle. One or more maintenance compositions may be orally administered. The maintenance composition may include blueberry fiber and/or probiotics.

Implementations may include one or more of the following features. In some implementations, one or more cleanse compositions and one or more renew compositions may be orally administered. The cleanse compositions may include magnesium sulfate and/or fruit juice. The fruit juice may include blueberry juice, grape juice, and/or green tea. The cleanse composition or portions thereof may be administered at a warm temperature (e.g., above room temperature and/or above body temperature). The renew composition may include fiber and/or probiotic. Administration of renew composition(s) after the administration of cleanse composition(s) may improve and/or maintain gastrointestinal health (e.g., lower gastrointestinal health) of an individual. The fiber in the maintenance and/or renew compositions may include comprises dried remnants of blueberries from blueberry juicing. The dental powder may include bismuth subsalicylate.

The details of one or more implementations are set forth in the accompanying drawings and the description below. Other features, objects, and advantages of the implementations will be apparent from the description and drawings.

BRIEF DESCRIPTION OF THE DRAWINGS

For a more complete understanding of this disclosure and its features, reference is now made to the following description, taken in conjunction with the accompanying drawings, in which:

FIG. 1 illustrates an implementation of an example process for promoting health.

DETAILED DESCRIPTION

Promoting oral and intestinal health has been commonly treated as two separate problems with two different solutions. Dental professionals tend to dental health without maximizing the benefits that can be received by the other portions of the gastrointestinal tract. However, there is a correlation between oral and intestinal health that has not yet been recognized within the health professional community. This association can be leveraged to promote (e.g., improve and/or maintain) intestinal health via treatments of the mouth and promotion of healthy mouth flora. Promotion of the health of the mouth and healthy mouth flora is not merely the same as taking commercially available oral probiotic capsules such as Culturelle (commercially available from i-Health, Inc., Cromwell, CT), but is specific treatment of the mouth.

In addition, improving and/or maintaining oral health can improve and/or maintain overall health. It has been shown, in scientific studies, that improvement of the integrity of the oral flora can provide benefits to the upper respiratory tract (e.g., by preventing infections). Furthermore, while links between oral/periodontal health and cardiac and peripheral vascular health have been discovered, the link between improvements of oral flora health and/or eradication of certain oral organisms leading to benefits of cardiac and vascular health (e.g., via herein described systems and methods), has not been previously proved. The prior art fails to study or propose that improvements to oral, dental, and periodontal health (e.g., improvements to the oral flora) provide improvements in gastrointestinal health and/or flora integrity, as provided herein. In various implementations, the described oral compositions may be administered to improve overall health (e.g., upper respiratory tract, cardiac, and/or vascular).

Oral compositions may be administered to improve or maintain the health of the gastrointestinal tract or portions thereof (e.g., oral and/or intestinal). The administration of the oral composition may decrease inflammation and/or improve flora. Administration of the oral composition may improve and/or inhibit diseases in the gastrointestinal tract and/or reduce symptoms of diseases and/or disorders in the gastrointestinal tract (e.g., by reducing oral and/or intestinal inflammation). The administration of the oral composition may improve lower gastrointestinal tract health greater than expected due to the effect of improved oral flora on the gastrointestinal tract. For example, as bacteria in the mouth are continuously delivered down the gastrointestinal tract via swallowing, thus improvement in the oral flora via the oral compositions will improve gastrointestinal health more than delivery of a probiotic directly to the lower gastrointestinal tract by improving the quality of bacteria delivered in swallowing. The oral compositions may be used separately and/or in conjunction with intestinal compositions (e.g., described intestinal compositions).

Oral compositions may include a dental powder, a toothpaste, a mouthwash, and an oral probiotic composition. The oral composition(s) may be administered separately, in conjunction with each other, and/or in conjunction with other oral compositions.

The dental powder may whiten teeth, reduce cavities by reducing the amount of harmful bacteria present in a mouth and/or increasing good flora in the mouth, improve gastrointestinal health (e.g., mouth, and/or intestinal health), and/or improve user health, in some implementations. The dental powder may reduce inflammation (e.g., locally), inhibit and/or treat gingivitis, inhibit acid erosion, inhibit and/or treat periodontitis, and/or otherwise improve oral health. The dental powder may include the dental powder as described in U.S. Pat. No. 9,884,010 entitled "Dental Hygiene Systems", U.S. patent application Ser. No. 15/889,190 entitled "Dental Hygiene Systems", or portions thereof. The dental powder may be granular (e.g., average particle size of approximately 10 microns to approximately 100 microns) to at least partially abrade one or more surfaces of a user's teeth (e.g., without substantially damaging the enamel of the teeth). The dental powder may include an antacid powder. The antacid powder may be at least partially consumed to provide antacid effects to the stomach. The dental powder may include any appropriate basic salt. For example, the dental powder may include one or more basic mineral salts that include calcium carbonate, magnesium carbonate, zinc, and/or other similar compounds. For example, the dental powder may include dolomite, a natural occurring mineral containing these salts, and/or predetermined combinations of calcium carbonate and/or magnesium carbonate (e.g., isolated calcium carbonate and/or isolated magnesium carbonate). The dental powder may include a first compound with a stoichiometric ratio of approximately 1:1 to approximately 3:1 of calcium to magnesium.

The dental powder may include one or more probiotics, in some implementations. Any appropriate probiotics may be utilized in the dental powder. In some implementations, an anti-cavity probiotic (e.g. a probiotic that inhibits cavities and/or bacteria growth that causes cavities) may be included, such as a *Streptococcus salivarius*. For example, the dental powder may include *Streptococcus salivarius* M-18 and/or *Streptococcus salivarius* K-12. In some implementations, one or more other additional probiotics may be included such as probiotics to develop good oral flora and/or decrease halitosis symptoms. For example, one or several *Lactobacillus* strain(s) of probiotics In some implementations, the dental powder may include a strain of *Streptococcus salivarius* but not other probiotics such as *Lactobacillus* to allow the *Streptococcus salivarius* to culture in the mouth and overcome other microorganisms within the mouth. In some implementations, bacteria associated with healthy intestinal flora may be utilized and may unexpectedly produce healthy flora in oral regions.

In some implementations, the dental powder may include fiber. For example, fiber derived from blueberries and/or other appropriate types fiber may be included in the dental powder. The fiber derived from blueberries, Blueberry Fiber, may include the dried skins, seeds, and pulp or portions thereof. For example, the Blueberry Fiber may be obtained by drying the remains from removing the juice from blueberries. The Blueberry Fiber may be ground to a predetermined granularity, in some implementations. The dental powder may include any appropriate amount of fiber. In some implementations, the dental powder may include approximately 0.1 g-approximately 1 g of fiber and/or approximately 0.1 g to approximately 1 g of probiotic. The dental powder may include approximately 0.4 g-approximately 0.6 g of fiber and/or approximately 0.4 g-approximately 0.6 g of probiotic. The dental powder may include approximately 1: approximately 1 ratio of fiber to probiotic, in some implementations.

The fiber in the dental powder may increase the promotion of healthy flora in the gastrointestinal tract. In some implementations, the bacteria in the mouth and/or intestines may consume the fiber or portions thereof, which may cause the bacteria to multiply and thus promote healthy flora. In some implementations, the dental powder may include blueberry fiber (e.g., derived from blueberries), which may provide anti-inflammatory properties, antioxidant properties, and/or selective antiseptic properties to the gastrointestinal tract (e.g., oral and/or intestinal). For example, as a user applies the dental powder to the teeth and gums (e.g., by brushing), the blueberry fiber may reduce inflammation in the oral cavity (e.g., gums) and/or kill or damage bacteria associated with unhealthy oral flora.

A dental powder including fiber may or may not include probiotics. The dental powder may include probiotics and fiber to promote growth of one or more strains of bacteria in the probiotics. In some implementations, the dental powder may include fiber and not include probiotics to promote existing healthy mouth flora (e.g., as a maintenance product) and/or since probiotics are being applied to the oral cavity via other appropriate methods.

In some implementations, the dental powder may include one or more other compounds such as minerals, essential oils, medicinal herbs (e.g., Western herbs and/or Chinese herbs), blueberry fiber, and/or bismuth subsalicylate. For example, essential oils may include, but are not limited to, oils of peppermint, wintergreen, eucalyptus, red thyme, white thyme, frankincense, bergamot, myrrh, clove, and lavender; herbs known to be antiseptic and/or anti-inflammatory, herbs known to promote oral and gastrointestinal tissue integrity, turmeric, parsley, oregano, sage, and/or green tea extract. Medicinal herbs may include, for example, myrrh, chaparral, parsley oil, Echinacea, goldenseal, xylitol, gotu kola, kola, other appropriate herbs, and/or combinations thereof. A dental powder that includes medicinal herbs may reduce odor (e.g., in the mouth), improve tissue health (e.g., when compared to not using the composition), improve mouth health (e.g., when compared to not using the composition) and/or provide antiseptic, anti-inflammatory, tissue healing, antibacterial, and/or other appropriate qualities to the dental powder. The quantity of the herbs (e.g., myrrh, chaparral, parsley oil, Echinacea, goldenseal, xylitol, gotu kola, kola, other appropriate herbs, and/or combinations thereof) administered may be an effective amount for mouth health. In some implementations, the dental powder (e.g., as a powder and/or toothpaste) may include one or more essential oils of peppermint, wintergreen, red thyme, eucalyptus, basil, bergamot, clove, pine needle, frankincense, juniper berry, sage, myrrh, gotu kola, Echinacea purpurea, Echinacea angustifolia root, chamomile flower, white sage, aloe vera leaf, goldenseal root, and/or myrrh gum resin. The quantity of these herbs administered may not exceed maximum daily and/or yearly amounts (e.g., as provided by the US FDA or other regulatory agency). In some implementations, the toothpaste may include garlic, which may inhibit symptoms of halitosis.

In some implementations, the dental powder may include bismuth subsalicylate (e.g., with and/or without other described compounds including calcium, magnesium, probiotics and/or other compounds). Bismuth subsalicylate may be utilized to treat and/or inhibit periodontitis and/or otherwise improve overall health. When the bismuth subsalicylate is applied (e.g., brushed) to a user's mouth or portions thereof, the bismuth subsalicylate may act as an anti-inflammatory and/or exhibit antibiotic-like properties. The Bismuth subsalicylate may reduce the growth of undesirable bacteria in the mouth and may reduce inflammation in the mouth and/or gastrointestinal tract (e.g., if the toothpaste is consumed). For example, the bismuth may inhibit growth of anaerobic bacteria in the mouth that may contribute to periodontitis. The subsalicylate may act as an anti-inflammatory to treat inflammation caused by periodontitis, in some implementations. Reducing inflammation in the mouth may treat symptoms of diseases such as gingivitis and/or periodontitis. Reducing overall inflammation in the body (e.g., including the mouth) may relieve and/or reduce symptoms of other inflammatory diseases (e.g., allergies, food insensitivities, arthritis, cardiovascular and peripheral vascular disease, etc.). In some implementations, a dental powder that includes approximately 100 mg to approximately 750 mg of bismuth subsalicylate may be administered (e.g., applied to the user's mouth). For example, the dental powder that includes bismuth subsalicylate may be administered approximately 1 to 5 times a day (e.g., after meals, upon waking, before bed, etc.). The amount of bismuth subsalicylate administered may not exceed approximately 2 grams daily, in some implementations.

In some implementations, the dental powder (e.g., as a powder and/or toothpaste) may include bismuth subsalicylate and one or more essential oils of peppermint, wintergreen, red thyme, eucalyptus, basil, bergamot, clove, pine needle, frankincense, oregano, juniper berry, sage, myrrh, gotu kola, Echinacea purpurea, Echinacea angustifolia root, chamomile flower, white sage, aloe vera leaf, goldenseal root, myrrh gum resin, and/or garlic. In some implementations, the mouthwash including bismuth subsalicylate may be administered in individuals with, susceptible to, and/or in pre-stages of developing periodontitis. The bismuth subsalicylate and/or included essential oils (e.g., garlic) may reduce inflammation and decrease the quantity of bad flora in the mouth.

In some implementations, a dental powder including bismuth subsalicylate may be administered in individuals with, susceptible to, and/or in pre-stages of developing periodontitis and a dental powder without bismuth subsalicylate may be otherwise administered (e.g., to individuals without periodontitis).

The dental powder may be provided in any appropriate delivery form, as described in U.S. patent application Ser. No. 15/096,489. In some implementations, the dental powder may be provided in portioned containers, such as sealed conduits (e.g., sealed flexible and/or inflexible straws), sachets (e.g., plastic, paper, foil, etc.), and/or any other appropriate delivery form. The dental powder may be provided in tablets (e.g., to dissolve in the mouth and/or chew) and/or capsules.

The dental powder may be applied to (e.g., brushed onto) at least a portion of the teeth and/or at least a portion of the gums of a user's mouth. By brushing the dental powder into the teeth and/or gums, the probiotics of the dental powder may be forced into gums and/or around the mouth to allow the probiotics to spread and/or grow in the mouth. The probiotics may be desiccated and/or dormant. The probiotics may be partially revived by saliva in the mouth. In some implementations, the dental powder may be administered by mixing the dental powder in a hydrating solution (e.g., water) to allow a user to swish and/or swallow the dental powder solution. The dental powder solution administration may provide an antacid mechanism (e.g., in the region of the teeth and/or gums) and/or provide nutritional supplementation (e.g., calcium, magnesium and/or probiotics) to portions of the gastrointestinal tract. In some implementations, at least a portion of the probiotics in the dental powder may be ingested and may be provided to the intestinal tract to promote good flora development in the intestinal tract.

In various implementations, an oral composition may include a toothpaste. The toothpaste may be any appropriate toothpaste. The toothpaste may not include an antibiotic and/or antibacterial agent, in some implementations, such that growth of the probiotics deposited in the mouth by the dental powder is encouraged. The toothpaste may include Bismuth subsalicylate. The toothpaste may include, in some implementations, a base of calcium and/or magnesium minerals and/or a base of elements derived from the earth and/or kaolin.

The toothpaste may be applied using a toothbrush (e.g., manual and/or electric) to the teeth and/or gums of an individual. In some implementations, the toothpaste and the dental powder may be applied concurrently. For example, a container may dispense the toothpaste and dental powder together. In some implementations, toothpaste may be applied to the brush and the dental powder may be applied to the toothpaste (e.g., by dipping the toothbrush into dental powder, sprinkling dental powder on the toothpaste, etc.) and/or vice versa. The toothpaste may be brushed into teeth and gums to apply the toothpaste to various regions of the mouth and/or dislodge food particles from the teeth and/or mouth. The toothpaste may be spit out and/or at least partially swallowed after brushing.

The oral compositions may include a mouthwash, in some implementations. The mouthwash may not include antibacterial and/or antiseptic agents (e.g., such that the probiotics applied in the dental powder and/or healthy oral flora are not killed by the mouth wash), in some implementations. The mouthwash may include Bismuth subsalicylate (e.g., to reduce inflammation and/or to provide a local antibacterial effect). The mouthwash may include may be flavored with essential oils, including but not limited to oils of peppermint, wintergreen, eucalyptus, red thyme, white thyme, frankincense, bergamot, myrrh, clove, lavender. The mouthwash may contain extracts of herbs known to be antiseptic and/or anti-inflammatory, and/or known to promote oral and gastrointestinal tissue integrity including but not limited to, Gotu kola, kola, Echinacea, turmeric, parsley, oregano, and/or sage, green tea extract, and/or certain herbs (e.g., Chinese herbs) known to have these beneficial health effects from their use. The flavorings may have anti-inflammatory effects, in some implementations. For example, the mouthwash may include one or more essential oils of peppermint, wintergreen, red thyme, eucalyptus, basil, bergamot, clove, pine needle, frankincense, juniper berry, sage, myrrh, gotu kola, chaparral, goldenseal root, chamomile flower, and licorice. As another non-limiting example, the mouthwash may include bismuth subsalicylate and one or more essential oils of peppermint, wintergreen, red thyme, white thyme, eucalyptus, basil, bergamot, clove, pine needle, frankincense, oregano, juniper berry, sage, myrrh, gotu kola, chaparral, goldenseal root, chamomile flower, licorice and garlic. In some implementations, the mouthwash including bismuth subsalicylate may be administered in individuals with, susceptible to, and/or in pre-stages of developing periodontitis. The bismuth subsalicylate and/or included essential oils (e.g., garlic) may reduce inflammation and decrease the quantity of bad flora in the mouth. In some implementations, the mouthwash may be a liquid form of the toothpaste and/or a portion thereof. For example, the mouthwash may be the toothpaste mixed with water.

Gargling and/or rinsing a mouth with mouthwash may remove food particles from the mouth (e.g., released by brushing with the dental powder and/or toothpaste), disperse the mouthwash through the mouth, reduce the numbers of undesirable bacteria and microorganisms present, and/or reduce inflammation.

The oral compositions may include an oral probiotic composition, in some implementations. The oral probiotic compositions may include one or more probiotics that promote oral health, upper respiratory health, and/or intestinal health. For example, the probiotic may include one or more predetermined strains of bacteria (e.g. *Lactobacillus* species, *Bifidobacterium*, non-pathogenic Streptococci). As another example, the oral probiotic composition may include *Streptococcus salivarius* BLIS K12™ and one or more other probiotics such as *Lactobacillus rhamnosus, Lactobacillus paracasei, Lactobacillus plantarum, Lactobacillus reuteri*, and/or *Lactobacillus salivarius*. The oral probiotic composition may include at least 6 billion active cultures per dose (e.g., powder or tablet dose).

In some implementations, the bacteria to include in the oral probiotic composition may be selected to maintain and/or improve upper gastrointestinal tract health. For example, the oral probiotic composition may include *Streptococcus salivarius* BLIS K12™ and one or more other probiotics such as *Lactobacillus rhamnosus, Lactobacillus plantarum, Lactobacillus reuteri*, and *Lactobacillus salivarius*. This oral probiotic composition may improve mouth and/or upper intestinal tract. This oral probiotic may be in an immediate release delivery form (e.g., immediate delivery capsule, foil packet with probiotic blend, etc.).

The oral probiotic may be provided in any appropriate delivery form such as sachets (e.g., paper, plastic, foil), sealed conduits (e.g., straws sealed at both ends), capsules, tablets, etc. The oral probiotic may be administered by topically applying the oral probiotic composition to the mouth (e.g., via toothbrush, placing in the mouth, etc.), and allowing the probiotics in the probiotic composition to disperse in the mouth (e.g., by allowing a tablet to dissolve, chewing a tablet, swishing the probiotic around in the mouth, etc.). The oral probiotic may be swallowed after application to a mouth.

In some implementations, by inhibiting the introduction of antibacterial and/or antiseptic agents in oral compositions, such as the dental powder, mouthwash, and/or toothpaste, while promoting healthy flora, an individual's overall health may be maintained and/or improved. Since a healthy mouth flora may be reduced and/or eliminated by periodic use of antibacterial and antiseptic products, the use of oral compositions without antibacterial and antiseptic products may promote healthy oral flora, which may promote healthy intestinal flora and/or provide other health benefits (e.g., respiratory and/or cardiovascular).

In various implementations, one or more of the oral compositions may be provided as a kit. For example, a kit may include the dental powder, a toothpaste, and/or a mouthwash. Individuals may use one or more of the oral compositions concurrently and/or sequentially to promote healthy mouth flora, inhibit the symptoms of halitosis, reduce or inhibit gingivitis, reduce or inhibit periodontitis. For example, an individual may brush teeth with the dental powder and/or toothpaste and follow with a mouthwash. In some implementations, probiotics of the oral compositions may be administered via the dental powder, toothpaste and/or mouthwash.

Since, although previously unrecognized, the flora of the mouth affects the flora of the intestinal tract, promotion of good flora in the mouth may promote the growth of good flora in the intestinal tract. Thus, as an individual swallows saliva with bacteria associated with good flora, at least a portion of the bacteria associated with good flora may pass to the intestines and promote growth of good flora in the intestines. A healthy mouth flora (e.g., promoted via one or more of the oral compositions) may act as a probiotic supplement for the intestines since an individual swallows a plurality of times a day allowing the healthy mouth flora to slowly supplement the flora of the intestinal tract. Thus, costs associated with daily probiotic supplements may be decreased since lower dosages of probiotics may be administered and/or frequency of administration may be reduced. By the same token, administration of such products may prevent the presence and growth of bad bacteria, which if left uninhibited, will further colonize the intestinal tract during repeated and regular swallows of saliva.

In various implementations, intestinal compositions may be administered to improve and/or maintain health of at least a portion of the gastrointestinal tract, such as the intestines. As opposed to oral compositions that are topically applied to the mouth and may or may not be swallowed, intestinal compositions are swallowed and delivered to the lower gastrointestinal tract. For example, the intestinal compositions may include fluids (e.g., gels, liquids, solids mixed with liquids, etc.) that are swallowed to deliver to the stomach and intestines. The intestinal compositions may be administered via delivery vehicles (e.g., capsules) that are selected such that the compositions may be released at a predetermined areas of the gastrointestinal tract (e.g., lower gastrointestinal tract, in stomach, after stomach, colon, etc.).

In some implementations, the intestinal compositions may include a cleanse composition, a renew composition, and/or an intestinal maintenance composition. One or more of the intestinal compositions may be orally administered, as appropriate, to improve or maintain gastrointestinal health. The intestinal composition(s) may be administered with (e.g., at the same time, at the same period of time, subsequent to, before, etc.) and/or without oral composition(s).

The cleanse composition may be capable of cleansing the entire gastrointestinal tract of its contents as a desired and intended effect. For example, prior to medical and/or surgical procedures, such as colonoscopies and/or gastrointestinal tract surgeries gastric bypass, resection of any part of the intestine, etc.), the cleanse composition may be administered to cleanse a bowel of a patient undergoing the procedure. In some implementations, the cleansing composition may be administered to other individuals, who may desire a bowel cleansing (e.g., after illness, to maintain health, to prevent, reduce, or eradicate systemic inflammatory disease such as arthritis, etc.). For example, some individuals with colitis may experience symptom relief after a cleanse. However, current commercially available cleanses are either harsh and inappropriate for repeat usage, restricted to use in a medical setting, fail to completely cleanse (e.g., lemon cleanses, colonic), and/or take a long time to achieve a cleanse (e.g., a week). The described cleanse may provide a gastrointestinal cleanse (e.g., suitable for gastrointestinal tract surgery, for renewal with renew compositions, and/or for reduction of symptoms in individuals with gastrointestinal problems) that is functional (e.g., provides a full or almost full cleanse rather than just a partial cleanse) within a short period of time (e.g., less than approximately 24 hours, less than 48 hours, etc.).

The cleanse composition may include any appropriate form of magnesium sulfate. For example, the cleanse composition may include a hydrate of magnesium sulfate, such as magnesium sulfate heptahydrate. For example, the cleanse composition may include Epsom salt. In various implementations, a hydrate of magnesium sulfate is utilized since it can be mixed with water based solutions, such as juice. For example, magnesium sulfate does not mix well with water and generates excessive heat when mixing is attempted. Thus, use of a hydrate of magnesium sulfate may increase user satisfaction (e.g., since warm/hot fluids may be unpalatable to some users, since consumption of the cleanse composition may be difficult if a portion is not well mixed) and/or reduce manufacturing costs (e.g., reduced need for binders due to poor mixing, increased production costs to bind poorly mixing compounds, etc.). In some implementations, the cleanse composition may be provided at a warm temperature (e.g., greater than room temperature and/or body temperature). The warm temperature may increase the movement of stool and fluids in the gastrointestinal tract, The cleanse composition may include fluid, such as juice, and/or a sweetener. For example, apple, grape, blueberry, plum, mango, strawberry, acai berry, and/or any other appropriate fruit juice may be utilized. In some implementations, other fluids such as water may be utilized. Fluids that aggravate symptoms of a cleanse may not be utilized (e.g., alcohol which may increase dehydration). The juice (e.g., blueberry and/or grape) selected as a fluid for combination with the hydrate of magnesium sulfate may have properties of an osmotic laxative. Hydrates of magnesium sulfate have a bitter taste that is difficult to mask. The juice and sweetener may increase palatability during administration. In some implementations, a blend of more than one juice may be utilized. The complexity of flavor present with a blended juice may mask flavors more than a single ingredient juice (e.g., apple), in some implementations. The juice may increase cleansing properties of the cleansing composition. For example, blueberry and/or grape juice may increase the laxative properties, and thus the cleanse properties, of the hydrate of magnesium sulfate, in some implementations.

In some implementations, the use of a blended of blueberry and grape juice may increase user satisfaction with the cleanse composition since the blended juice may increase palatability (e.g., by mask the flavors of the hydrate of magnesium sulfate and/or providing a pleasant tasting cleanse composition) and/or increase the cleansing properties. The use of blueberry juice may improve the flushing of the gastrointestinal tract by providing selective antiseptic properties. Thus, the blueberry juice may kill, impair, and/or inhibit growth of one or more bacteria strains associated with unhealthy gastrointestinal flora.

In some implementations, the cleanse composition may include a fluid such as green tea, in addition to and/or instead of juice. The cleanse composition may include green tea powder. In addition, the gently naturally caffeinated green tea ingested (e.g., as a hot drink) may stimulate intestinal peristalsis, facilitating passage of the osmotic laxative through the intestinal tract, with the benefit of a more rapid transit and therefore, more effective cleansing action.

The sweetener in the cleanse composition may include any appropriate sweetener. For example, the sweetener may include sugar (e.g., honey, cane sugar, beet sugar, etc.) and/or sugar substitutes (e.g., saccharin, stevia, sorbitol, xylitol, lactulose, lactitol, sucralose, etc.). In some implementations, a sugar substitute may be utilized to sweeten the cleanse composition since sugar may aggravate adverse side effects of the cleanse composition.

In some implementations, the cleanse composition may include approximately 20 cc to approximately 40 cc of a powder form of a hydrate of Magnesium sulfate. The cleanse composition may include at least approximately 3 ounces of juice. The cleanse composition may include at least 2/16 teaspoon of sweeter. For example, a cleanse composition may include approximately 30 cc of powdered magnesium sulfate heptahydrate (e.g., approximately 1 ounce) mixed with approximately 4 ounces to approximately 5 ounces of juice. The juice may include a blend of grape(s) (e.g., Muscadine grape) and blueberry juice. Sweetener may be added, for example, approximately 3/16 to approximately 1/4 teaspoon of stevia extract powder may be added and mixed with the hydrate of magnesium sulfate and juice.

The cleanse composition may be administered orally. For example, a user may drink the cleanse composition. During administration of the cleanse composition, an individual's diet may be restricted. For example, the individual may not consume solid or liquid foods. The individual may be restricted from drinking fluids other than water, in some implementations. The cleanse composition may be administered once or twice, in some implementations. For example, if approximately 4 to approximately 6 hours after administration of a first dosage of the cleanse composition, fluids leaving the gastrointestinal tract are not clear, one or more additional dosages may be administered, as appropriate. The cleanse composition may be capable of cleansing a bowel in less than 24 hours. In some implementations, the cleanse composition may be capable of cleansing the bowel in less than 6 hours. In some implementations, the cleanse composition may include magnesium sulfate (e.g., hydrate of magnesium sulfate) and blueberry juice. The cleanse composition may include grape juice and green tea. The combination of the magnesium sulfate and blueberry juice may provide a faster and more efficient cleanse than just each would singularly administered. The combination of the magnesium sulfate, fruit juice, and green tea may provide a faster and more efficient cleanse than just each would singularly administered. For example, a cleanse may be achieved within 24 hours. In some implementations, the cleanse composition may be administered in more than one dose (e.g., the magnesium sulfate and fruit juice may be delivered in one dose and the green tea may be delivered in another dose; the magnesium sulfate and green tea may be delivered in one dose and the fruit juice may be delivered in another dose, etc.).

The cleanse composition may strip at least a portion and/or, often, most of the microorganisms in the lower intestinal tract. The cleanse composition may strip microorganisms via the fluid movement through the gastrointestinal tract and/or via the selective antiseptic properties of the blueberry juice. Thus, the administration of the cleanse composition may be followed by administration of the renew composition and/or the maintenance composition. By flushing the gastrointestinal tract prior to administering the renew composition, the probiotics of the renew composition may more readily grow in the gastrointestinal tract (e.g., since the probiotics have less competition by the lower number of other bacteria and by the presence of less bacteria associated with unhealthy flora).

In some implementations, the cleanse composition may include magnesium sulfate (e.g., hydrate of magnesium sulfate) and blueberry juice. The cleanse composition may include grape juice and green tea. The combination of the magnesium sulfate and blueberry juice may provide a faster and more efficient cleanse than just each would singularly administered. The combination of the magnesium sulfate, fruit juice, and green tea may provide a faster and more efficient cleanse than just each would singularly administered. For example, a cleanse may be achieved within 24 hours.

The renew composition may promote healthy intestinal flora in an individual. The renew composition may be administered orally. For example, an individual may ingest (e.g., drink and/or eat) the renew composition. The renew composition may include a fiber component and one or more probiotics. The renew composition may include a fluid (e.g., fiber and a liquid) and separate delivery form for a probiotic (e.g., capsule, tablet, foil package, etc.), in some implementations. The fiber component may promote growth of healthy flora in the gastrointestinal tract (e.g., oral and/or intestinal).

In some implementations, the fiber may include a fruit-derived fiber (e.g., fiber from fruit). The blueberry or other fruit-derived fiber component may promote growth of healthy flora in the oral cavity and/or intestinal tract. For example, the fiber component may promote growth and/or establishment of a colony of the probiotics in the renew composition in the intestinal tract. Its addition to the oral dental powder or oral probiotic formulation would have the same effect and purpose.

The fiber component of the renew composition may include any appropriate fiber. The fiber component may include synthetic and/or natural fiber products. The fiber component may include lignin, cellulose, pectin, psyllium, polydextrose, polyols, maltodextrins, and/or combinations thereof, in some implementations.

In some implementations, the fiber component may include fiber from fruits and/or vegetables. The fiber component may include fiber derived from blueberries (e.g., blueberry fiber). In some implementations, blueberry juice may be extracted from blueberries and the remaining portions of the blueberry may be utilized for the fiber component. These remaining portions may include the skins, pulp, seeds, etc. from the blueberries. The remaining portions may be dried and/or reduced in particle size (e.g., ground, crushed, cut, and/or pulverized) to produce a blueberry fiber component. The use of the remaining portions from juicing (e.g., skins, pulps, seeds, etc.) may provide benefits when compared with the use of husks. The use of the skins, seeds, and pulps may include antioxidants, such as resveratrol and/or other antioxidants, and/or fiber in greater quantities than the merely the husks. In some implementations, costs may be reduced in the manufacturing of the oral and/or intestinal compositions since fruit juice and fruit derived fiber may both be utilized (e.g., blueberry juice and blueberry fiber)

This blueberry fiber may have selective antiseptic properties. The blueberry fiber may inhibit organisms in unhealthy flora such as yeast that are considered bad for the gastrointestinal tract. However, the blueberry fiber may not act as an antiseptic that inhibits growth of one or more bacteria in the probiotic and/or one or more bacteria associated with healthy flora. The blueberry fiber may be used in place of FOS (Fructooligosaccharides) and/or inulin, in some implementations, since blueberry fiber may promote growth of bacteria (e.g., in probiotics and/or in healthy flora). The use of blueberry fiber may provide a natural component and/or fewer side effects than FOS (Fructooligosaccharides) and/or inulin, in some implementations.

This blueberry fiber component may be more tolerated (e.g., less undesirable side effects when compared with psyllium), more flavorful, less expensive (e.g., when blueberry juice and blueberry fiber are utilized) and/or increase user satisfaction (e.g. since the product is composed of naturally consumed produce and/or may be more environmentally friendly since less waste is produced). This process may be utilized with other fruits to create other natural fiber components for use in the renew composition. For example, grape juice may be extracted from grapes and the remaining portions of the grape (e.g., skins, pulp, and/or seeds) may be processed to produce a grape fiber. The remaining portions of the grape may be dried and/or reduced in particle size. In some implementations, the juice and/or remaining portion of other fruits and/or vegetables such as apricots, carrots, mangos, apples, etc. may be utilized in the cleanse composition and/or the renew compositions.

The fiber component (e.g., in oral and/or intestinal compositions) may include blueberry fiber (fiber derived from blueberries), in some implementations. The blueberry fiber may increase health in unhealthy individuals, such as individuals with constipation and/or diarrhea. The mucilage of the blueberry fiber may have the unique ability to hold water in individuals with constipation and absorb water in individuals with diarrhea. Thus, in addition to promoting growth of bacteria in the gastrointestinal tract (e.g., from a probiotic administered), encouraging establishment of bacteria from a probiotic administered, and/or the ability to act generally as a fiber component, the blueberry fiber may make users feel better due to its affect on individuals with constipation and/or diarrhea. Since a portion of users that are administered cleanses have underlying gastrointestinal problems (e.g., such as constipation and/or diarrhea), the blueberry fiber may provide additional relief.

In some implementations, the fiber component may include approximately 1 to approximately 2 tablespoons of the fiber component (e.g., per administration). In some implementations, the fiber component may include less than approximately 4 tablespoons (e.g., per administration). In some implementations, the amount of fiber included in a dosage may be based on the administration schedule (e.g., such that less than approximately 4 tablespoons of fiber component is administered daily).

The renew composition may include one or more probiotics. Any appropriate probiotic (e.g., that promotes gastrointestinal health) may be utilized. The bacteria of the probiotic may be capable of overcoming the growth of the less healthful and/or undesirable bacteria. When the previously existing bacteria are in lower magnitudes and/or die (e.g., due to administration of the cleanse), the intestinal tract may be more susceptible to entrenchment and/or growth of bacteria. However, without the introduction of an additional change, such as the administration of a renew composition, the existing bacteria left after the cleanse will continue to grow. The administration of renew composition(s) may allow microorganisms associated with a healthy intestinal flora to grow. For example, by administering the renew composition, the probiotics or a portion thereof may be deposited into the intestinal tract. In some implementations, at least a portion of the probiotic(s) in the renew composition may include desiccated and/or dormant probiotic, which may be revived by rehydration from the liquids (e.g., saliva) present in the user's gastrointestinal tract or a portion thereof, fluids consumed with the renew composition, a solution in which the renew composition is mixed, etc. The probiotics deposited in the intestinal tract may grow (e.g., binary fission). As the probiotics in the intestinal tract grow, other bacteria present in the area may exist in lower magnitudes and/or die (e.g., the colony may enter the death phase). When the previously existing bacteria are in lower magnitudes and/or die, gastrointestinal health (e.g., bloating, abdominal pain, diarrhea, constipation, etc.) may be increased (e.g., when compared with a cleanse without administration of a renew composition).

In some implementations, the renew composition may include a first set of high efficacy/potency probiotics and a second set of multi-strain probiotics. In some implementations, the renew composition may be administered in at least two dosages. For example, a first dose may include the high efficacy probiotics and the second dose may include the second set of probiotics. Thus, the second set of probiotics may not be at as high a disadvantage as when administering the second set of probiotics with the high efficacy probiotics when trying to establish in the gastrointestinal tract (e.g., since the properties of the high efficacy strain, such as species and/or magnitude delivered, may make it difficult to compete with for establishment and/or growth in the gastrointestinal tract).

The first set of probiotics of high efficacy strain(s) microorganisms. A high efficacy strain may include a strain is more effective at promoting a healthy flora than a similar amount of other strains and/or be able to colonize and be efficacious throughout the entire gastrointestinal tract. For example, a *Lactobacillus rhamnosus* such as *Lactobacillus rhamnosus* GG may be utilized as a high efficacy strain of probiotic. The first set of high efficacy probiotics may include large number of microorganisms. For example, the first set of probiotics may include greater than approximately 10 billion cultures and/or equal to or greater than approximately 30 billion cultures per administered dose. In some implementations, rather than a first set of probiotics including a high efficacy strain, the first set of probiotics may include a strain (e.g., strain such as those included in the second set of probiotics) in a magnitude greater than approximately 30 billion cultures per administered dose.

The second set of multi-strain probiotics may include more than one strain of probiotics. The strains of probiotics in the second set of multi-strain probiotics may be different from or include one or more of the same strains of the probiotics in the first set of high efficacy probiotics. The strains of probiotics in the second set of multi-strain probiotics may be selected to more specifically colonize the colon utilizing high efficacy/potency probiotic mixtures. Any appropriate set of probiotics may be utilized. For example, the probiotic may include one or more predetermined strains of bacteria (e.g. *Lactobacillus* species, *Bifidobacterium*, non-pathogenic Streptococci, *Oxalobacter formigenes*). The second set of probiotics may include bacteria from the same genus than the first set of probiotic of the renew composition (e.g., high efficacy strain). In some implementations, the second set of probiotics may include one or more *Lactobacillus* strains and one or more *Bifidobacterium* strains. For example, the probiotics may include *Lactobacillus acidophilus, Lactobacillus plantarum, Lactobacillus rhamnosus, bifidobacterium bifidus, Lactobacillus salivarius, Bifidobacterium bifandus, bifidobacterium lactic*, and/or *Bifidobacterium longum*. The probiotics may include one or more commonly administered probiotic organisms associated with healthy intestinal flora, in some implementations. The second set of probiotics may include greater than approximately 10 billion cultures and/or greater than approximately 30 billion cultures. In some implementations, the second set of probiotics may include at least approximately 6 billion cultures approximately 6 to approximately 8 billion cultures; approximately 8 billion cultures to approximately 10 billion cultures, etc.). The first set and/or the second set of probiotics may be administered using delivery vehicles to target portions of the gastrointestinal tract (e.g., colon, after the stomach, etc.). Methods such as enteric coating of the capsule may be utilized to facilitate delivery of the probiotic organisms into the lower intestinal tract alive, thereby avoiding the risk of a substantial amount of the probiotics being killed by stomach acid, bile, and/or enzymes in the duodenum and/or jejunum.

Utilization of the fast set of high efficacy probiotics and the second set of multi-strain probiotics may provide increased gastrointestinal health (e.g., intestinal health) more than the either component individually and/or an additive benefit expected, either by the combination of the organisms administered, or a combined intended delivery throughout the entire gastrointestinal tract (first delivery system/single high efficacy strain product) or specifically the lower small intestine and colon (second delivery system/combination product). For example, a healthy flora may be established more quickly than when using either set individually or more quickly than expected (e.g., greater than an additive benefit). Thus, in some implementations, the renew composition may include administration of both the first set of high efficacy probiotics and the second set of multi-strain probiotics (e.g., sequentially).

The renew composition may be administered via any appropriate delivery vehicle for oral administration, such as tablets (e.g., lozenges, chewable and/or for swallowing), capsules, filled conduits (e.g., sealed straw or conduit), packets (e.g., foil packets, plastic sachets, and/or paper packets), liquid solutions, etc. The renew composition or a portion thereof (e.g., probiotics) may be administered via a delayed release delivery vehicle (e.g., capsule). For example, the probiotic portion of the renew composition may be administered via an enteric coated capsule. The use of a delayed release delivery vehicle for the probiotics may inhibit substantial release of the probiotics until after stomach and/or may be inhibited from breaking down in the presence of gastric fluids. Thus, the probiotics may be delivered to the intestines or portion thereof (e.g., colon). Targeting delivery of the probiotics to the colon may improve and/or maintain gastrointestinal health, in some implementations. In some implementations, renew composition may include a liquid solution and/or be dissolved at least partially in a liquid solution. For example, the fiber component and/or probiotic component may be mixed with water and/or other appropriate liquids (e.g., fruit juice such as blueberry juice). The liquid solution may not substantially harm probiotics, in some implementations. For example, the liquid solution may not include alcohol since alcohol may injure and/or kill at least a portion of the probiotics in the cleanse solution.

The renew composition may be one part or multi-part. For example, the renew composition may be administered via more than one delivery mechanism. In some implementations, the fiber component of the renew composition may be administered separately from the probiotic component(s). For example, a first capsule(s) may include the fiber component and one or more additional capsule(s) may include probiotics. In some implementations, the fiber component and at least one probiotic may be included in the same delivery vehicle (e.g., capsule, sealed straw, packet, etc.).

In some implementations, the renew composition may be multi-step. For example, an individual may not be administered the first set of high efficacy probiotic concurrently with the second set of multi-strain probiotic. Administering a set of high efficacy probiotic concurrently with other less effective probiotic may inhibit the less effective probiotic from growing in the intestinal tract of the individual (e.g., since the high efficacy probiotic may grow too quickly for the less effective probiotic to establish a culture in the intestinal tract and/or since the high efficacy probiotic may inhibit growth of the less effective probiotic). The fiber component may be administered with (e.g., in the same or separate delivery vehicle) the first set of high efficacy probiotic and/or with the second set of multi-strain probiotic. In some implementations, a first fiber component may be administered approximately concurrently the first set of high efficacy probiotic and a second fiber component may be administered approximately concurrently with the second set of multi-strain probiotic. The first fiber component and the second fiber component may be similar or different.

The intestinal maintenance composition may include fiber and/or probiotics. The intestinal maintenance composition may include the same fiber and probiotic agents as the renewal composition (e.g., in the same or different dosages), in some implementations. The intestinal maintenance composition may include one or more digestive enzymes. For example, more than one vegetarian sourced digestive enzyme may be included in the intestinal maintenance composition. In some implementations, the digestive enzymes may facilitate breakdown (e.g., digestion) of starches, proteins, fats, cellulose, and/or fiber. The digestive enzymes may include amylase, protease, lactase, lipase, cellulose, maltase, hemicellulase. The amount of digestive enzyme may be an amount great enough to allow a single administration of the intestinal maintenance composition prior to and/or concurrently with a meal (e.g., as opposed to ingesting multiple intestinal maintenance composition dosages over the course of a meal).

The intestinal maintenance composition may be provided via any appropriate delivery vehicle. For example, the intestinal maintenance composition may be provided in a capsule at least partially capable passing to the intestinal tract. For example, the intestinal maintenance composition may be provided in an uncoated capsule.

In some implementations, at least a portion of the probiotics utilized in the renew and/or intestinal maintenance compositions may be generated using a probiotic growth kit provided to the user. The kit may include a starter culture. The probiotics in the starter culture may be based on the composition to be made using the probiotic kit. For example, when generating probiotics for a renewal composition (e.g., to replace and/or supplement probiotics in the renewal composition), one or more probiotics may be selected to promote a healthy intestinal flora. For example, the starter culture of the probiotic kit may include one or more probiotics in the second set of multi-strain probiotics (e.g. *Lactobacillus* species, *Bifidobacterium*, non-pathogenic Streptococci). In some implementations, the probiotics in the starter culture may include one or more probiotics in the intestinal maintenance composition (e.g., to supplement and/or replace probiotics in the intestinal maintenance composition). For example, the starter culture for the intestinal maintenance composition may include one or more of (e.g. *Lactobacillus* species, *Bifidobacterium*, non-pathogenic Streptococci, and/or any other appropriate probiotic.

The kit may include fiber and/or juice. For example, the described blueberry fiber may be utilized in the kit. The juice may include blueberry juice. In some implementations, highly fermentable juices such as grapes may not be utilized with the kit to inhibit alcohol formation (e.g., which may inhibit probiotic growth and/or kill existing probiotics). In some implementations, the user may mix the starter culture with juice and may not include fiber (e.g., the fiber may not be included in the growth mixture and/or may be added at a later stage prior to consumption). In some implementations, a user may select fiber and/or juice for use with the kit based on preference and/or administration schedule. For example, the user may select fiber for addition on some days and add juice on the same or different days. The user may initially use fiber and later use juice to grow probiotic cultures and/or vice versa, for example. In some implementations, fiber such as the blueberry fiber may be utilized (e.g., instead of and/or in addition to juice) to promote the growth of microorganisms that are associated with a healthy gastrointestinal flora. For example, since the described blueberry fiber promotes the growth of microorganisms associated with a healthy flora, the use of the blueberry fiber to promote growth of the probiotics may encourage the probiotics to grow in a similar fashion as in the intestines (e.g., encouraging growth of microorganisms associated with healthy flora and discouraging growth of unhealthy microorganisms).

A user may mix the starter culture with the fiber and an appropriate amount of water and/or juice, and allow the probiotics in the starter culture to reproduce. In some implementations, the amount of fiber included may be more than the amount of fiber for probiotic growth (e.g., a growth amount). At least a portion of remaining fiber may be delivered to the user as fiber when consuming the mixture (e.g., after a growth period). Thus, the renewal and/or intestinal maintenance composition with probiotics. For example, a user may mix the starter culture with 16 oz of juice in a growth container The user may mix the starter culture with fiber and water in a growth container. The growth container stay have a cap to limit the amount of air accessible by the bacteria in the container (e.g., to allow the probiotics to grow in an environment similar to the intestines of a human). The growth container may be any appropriate container with a lid and/or a specialized container adapted to be received by a growth device. The growth device may control and monitor the environment in which the growth device is disposed (e.g., to inhibit addition of harmful bacteria from the environment, to promote growth of probiotics to mimic a specific environment such as the intestines or a portion thereof, and/or to control a temperature in the growth container by adding and/or removing heat, etc.). The growth device may include timer(s) and/or labels (e.g., color changing to provide information, numbers, letters, etc.) to facilitate tracking of probiotic, growth. In some implementations, an indication of the level of the probiotics may be provided by an indicator (e.g., test strip on the growth container and/or separate from the growth container).

The probiotics may be allowed to grow a predetermined period of time (e.g., a range of times after which the concentration of probiotics is within a specified range). A user may then drink a portion (e.g., approximately half, less than half, more than half) while allowing a portion to remain in the growth container. The remaining portion may be of a size (e.g., include an concentration of probiotics) to allow regrowth (e.g., reproduction) of the probiotics to a predetermined concentration after the same or a different predetermined period of time. A user may add a second quantity (e.g., the same and/or different from the initial amount) of fiber and/or juice. In some implementations, the juice may have a pH (e.g., controlled by concentration, fruit selected for the juice, etc.) such that the juice does not kill or injure a substantial amount of the bacteria in the probiotic. When a user adds fiber to the remaining portion in the growth container, the user may add a quantity of fluid, such as water and/or juice. The probiotics may be allowed to regrow (e.g., reproduce and thus multiply). Thus, a predetermined range of concentrations of probiotics may be repeatedly regrown using the probiotic starter. By allowing generation of probiotics via the kit, user satisfaction may be increased. For example, costs may be decreased when following an administration schedule (e.g., fiber and/or juice may be less expensive than purchasing probiotic packages), freshness may be increased which may allow delivery of a greater mount of probiotics (e.g., since probiotics continuously die off), and/or user confidence in the purity of the probiotics may be increased since the user is generating in the probiotics at home, for example. In some implementations, use of the probiotic generation kit may allow customization for individuals. For example, if an individual has sensitivity to a particular fiber and/or juice, the culture and/or fluids added may be modified based on the sensitivity. In some implementations, the strains utilized in the culture and/or type of fiber and/or fluid utilized may be individualized based on whether an individual is healthy, post cleanse, and/or unhealthy (e.g., symptoms of colitis).

In some implementations, the growth container and/or device may be utilized to augment probiotics provided in renewal and/or intestinal maintenance compositions). For example, the user may grow a starter package (e.g. including starter culture, fiber, and/or juice that is concentrated or unconcentrated) in a growth container for a predetermined period of time prior to consumption. The growth time (e.g., predetermined period of time) may allow the probiotic concentration to increase to an augmented level and/or predetermined level.

A user may have more than one growth container with probiotics growing to allow consumption based on an administration schedule (e.g., rather than disrupting an administration schedule to allow probiotics to regrow). For example, a predetermined period of time may be approximately 3 days and a user may have 3 growth containers (e.g., with probiotics growing). The growth containers may include the same and/or different probiotics based on user preference and/or administration schedule.

In various implementations, the oral compositions and the intestinal compositions may be utilized together and/or separately. When the oral compositions are utilized with intestinal compositions (e.g., before, after, with, etc.), lower gastrointestinal healthy may be increased more than when the intestinal composition is utilized alone. The oral compositions and/or the intestinal compositions may be utilized in healthy and unhealthy individuals. In some implementations, the type of oral and/or intestinal composition utilized and/or the administration schedule (e.g., dosage and/or frequency) may vary based on whether the individual is healthy. For example, individuals with periodontitis and/or halitosis may utilize dental powders with bismuth subsalicylate. As another example, cleanse compositions and/or renewal compositions with blueberry fiber may be administered more frequently in individuals attempting to reduce symptoms of gastrointestinal problems (e.g., irritable bowel syndrome, colitis, inflammation of gastrointestinal tract, etc.).

In some implementations, the oral composition(s) may include a dental powder that includes any appropriate basic salt and/or bismuth subsalicylate. The dental powder may include one or more herbs and/or essential oils. In some implementations, toothpaste of the oral composition may include herbs and/or essential oils. A dental powder comprising basic salt may be utilized, as desired and/or per an administration schedule, to increase whiteness of teeth, reduce acid erosion, and/or improve dental health. A dental powder comprising bismuth subsalicylate and/or a toothpaste may include bismuth subsalicylate to decrease symptoms and/or inhibit periodontitis. The toothpaste and/or dental powder may be administered periodically, such as daily (e.g., in a similar topical manner as tooth brushing).

The oral composition (e.g., toothpaste, dental powder, mouthwash, etc.) may include an oral probiotic composition. The oral probiotic may be brushed (e.g., when in the dental powder and/or toothpaste) or swished and/or gargled in the mouth (e.g., when in the mouthwash) to orally and topically administer the oral probiotic. Swallowing an oral capsule that includes a probiotic is not the same as orally and topically applying the oral probiotic to the mouth since topically applying the oral probiotic may distribute the probiotics in the mouth and allow the probiotics to promote a healthy flora in the mouth (e.g., as opposed to biting a capsule or the capsule dissolving inadvertently while swallowing the capsule). The oral probiotic composition may include at least one bacteria that improves, maintains, and/or is associated with good oral health. For example, the oral probiotic may include *Streptococcus salivarius*. The oral probiotic may include a second set of bacteria (e.g., administered with and/or after the administration of the bacteria to improve or maintain oral health). This second set of bacteria may include more than one strain of *Lactobacillus* bacteria. The use of the *Streptococcus* and *Lactobacillus* strains may inhibit tolerance to promotion of good flora via the oral composition that might otherwise occur in an individual when single strains of bacteria are administered repeatedly over a period of time.

In some implementations, a daily oral administration may include topically applying a toothpaste and/or dental powder (e.g., sequentially and/or concurrently) and applying an oral probiotic (e.g., via a mouthwash and/or topically applying the oral probiotic). The oral compositions may be applied before, after, and/or during a cleanse and/or renew administration. The oral compositions may be applied before, after, and/or during maintenance composition administration.

In some implementations, cleanse and renew composition(s) administration may be performed in less than 48 hours (e.g., in approximately 24 hours).

In some implementations, one or more of the described compositions may be provided in a kit. The components for the kit may be selected based on a goal (e.g., maintenance of health, cleanse, etc.) and/or an administrative schedule. In some implementations, the kit may include one or more components and the user (e.g., health professional and/or individual ingesting compositions) may select which components to administer. The kit may include oral composition(s), cleanse compositions, renew compositions, and/or maintenance compositions. The kit may include a probiotic generation kit (e.g., starter culture, growth container, fiber, and/or juice). The kit may include components for the administration schedule. The kit may include more than one composition and more than one administration schedule and a user may select an administration schedule and select components of the kit based on the kit.

For example, the cleanse composition may be administered to an individual to allow a cleanse in less than approximately 24 hours. A first dosage of the cleanse composition may be administered to the user and a predetermined period of time may be allowed to lapse (e.g., at least approximately 4 hours, at least approximately 6 hours, at least approximately 8 hours). The individual may be administered additional dosages of the cleanse composition after the predetermined period of time elapses (e.g., approximately 6 hours), if the cleanse is not complete (e.g., fluids exiting the body are not clear).

After the cleanse (e.g., after the predetermined period of time has elapsed after the last dosage of cleanse composition administration), one or more of the renew compositions may be administered to the individual. For example, a first set of probiotics and the second set of probiotics of the renew composition may be administered sequentially. The first set of probiotics may be administered and then the second set of probiotics may be administered at least 8 hours after administration of the first set of probiotics. For example, the first set of probiotics may be administered in the morning and the second set of probiotics may be administered in the evening. In some implementations, the second set of probiotics may be administered prior to the first set of probiotics. The sets of probiotics may be staggered to promote growth of both sets of probiotics in the intestinal tract. In some implementations, the first set of probiotics may not be administered.

In some implementations, the renew composition may be administered at least twice a day. The renew composition may be administered for more than 24 hours. For example, the renew composition may be administered as a maintenance composition on the second day (e.g., after 24 hours).

In some implementations, the intestinal maintenance composition may be administered prior to one or more meals. In some implementations, the intestinal maintenance composition may be administered prior to meals based on the composition of the meal.

In some implementations, the cleanse and/or renewal (e.g., administration of the cleanse and/or renew compositions) may be administered at regular intervals (e.g., every 3 months, every 6 months, every 9 months, annually, etc.) and/or as desired by the user. In some implementations, the administration of the renew composition and/or the intestinal maintenance composition may be more frequent than the administration of the cleanse (e.g., to maintain and/or promote healthy intestinal flora).

In some implementations, the frequency at which an individual is administered the cleanse, renew, and/or maintenance compositions may decrease. The intestinal flora may evolve over time by administering cleanse, renew, and/or maintenance compositions such that the fitness of the intestinal flora increases and frequency of administration of the cleanse, renew, and/or maintenance composition to maintain this fitness decreases. For example, after multiple cycles and/or long term use of cleanse, renew, and/or maintenance compositions, the harmful bacteria in the intestinal flora of an individual may decrease such that the need for reseeding the intestinal flora with healthful flora decreases while the benefits of a healthy intestinal flora are reaped.

In some implementations, one or more of the described compositions may be administered to improve or maintain the more than one portion of the gastrointestinal tract (e.g., mouth-colon). For example, an oral probiotic and a renew composition may be administered to improve or maintain the upper and lower gastrointestinal tract. In some implementations, the oral probiotic may include a probiotic targeted to improving and maintaining oral health such as, *Streptococcus salivarius* BLIS K12™, and one or more other probiotics (e.g., 6 probiotics) that are appropriate for at least oral administration such as *Lactobacillus rhamnosus, Lactobacillus paracasei, Lactobacillus plantarum, Lactobacillus reuteri*, and *Lactobacillus salivarius*. The combination of the effectiveness of the delivery of probiotics targeted to upper and lower gastrointestinal tract to improve overall gastrointestinal tract health is unexpected. For example, the lower gastrointestinal health is improved more by administering the combination of the oral probiotic and the renew composition than by administering the renew composition alone. In some implementations, the use of combinations of probiotics may inhibit resistance to promotion of healthy flora commonly found when single strains are administered repeatedly over time (e.g., the body may resist the implantation of the probiotic bacteria, existing bad flora in the gastrointestinal tract may adapt to survive, etc.). The use of one or more different probiotics in an upper and lower tract probiotic composition (e.g., oral probiotic and renew composition) may inhibit resistance to promotion of healthy flora that may develop with repeat administration of a single or single type of probiotic. In some implementations, a high dose of probiotics may be utilized to facilitate promotion of a healthy flora (e.g., to have more bacteria from probiotics to compete with bacteria from unhealthy flora to increase the odds that bacteria from probiotics may establish themselves as the healthy flora).

In some implementations, a component of one or more of the described systems may include diet recommendation and/or modifications, Diet recommendations may be based on promoting and/or maintaining good flora, health statistics (e.g., blood pressure, cholesterol, etc.), individual's general feeling of health, etc. The diet recommendations may be based on testing (e.g., allergy and/or sensitivity testing; bodily fluid testing such as blood, fecal, and/or urine; genetic testing; and/or any other appropriate testing) and/or recommendations dietary studies, government, and/or industry groups). Adherence to diet recommendations may decrease the frequency of cleanse, renew, and/or maintenance prescribed.

The frequency of the administration cleanse, renew, and/or intestinal maintenance compositions may be based on the disease, disorder, and/or condition being treated. For example, if the cleanse is performed for a medical procedure (e.g., colonoscopy), the cleanse may not be repeated and/or repeated when the same or a different medical procedure is performed. In some implementations, the cleanse and/or renew may be performed for the treatment and/or management of arthritis flares (e.g., to reduce frequency and/or duration) and may be repeated on a predetermined schedule (e.g., periodically) and/or when symptoms appear.

In some implementations, one or more of the described systems may be utilized as in an autotransplantation kit. The autotransplantation system may include cleanse and renew compositions. The cleanse composition may be administered in an individual to remove (e.g., flush, kill, and/or replace) existing flora in the gastrointestinal tract or portions thereof. The cleanse composition may flush and/or promote fluid movement in the gastrointestinal tract in the anatomic direction (e.g., as opposed to colonies which introduce fluid in a counter-anatomic direction in an attempt to flush the gastrointestinal tract). The renew composition may be administered following the cleanse composition to add new bacteria (e.g., from the renew composition) associated healthy flora into the gastrointestinal tract. The new bacteria may replace, change, and/or promote healthy flora in the gastrointestinal tract. In some implementations, it may be difficult to transform flora in the gastrointestinal tract without a cleanse portion (e.g., since existing flora may be entrenched and large in numbers). For example, in unhealthy individuals, such as individuals with colitis, unhealthy flora may be entrenched and difficult to replace by mere addition of probiotics.

In some implementations the autotransplantation kit may target a portion of the gastrointestinal tract such as the colon and/or mouth. For example, the autotransplantation kit may include an oral cleanse composition (e.g., dental powder and/or mouthwash that includes an antiseptic and/or Bismuth subsalicylate that removes (e.g., flush, kill, etc.) at least a portion of the bacteria residing in the mouth. The oral probiotic composition may then be administered to facilitate growth of healthy flora via bacteria in the probiotic. The cleanse administration may facilitate replacement of existing bacteria and/or promote healthy flora in unhealthy individuals (e.g., individuals with many cavities, halitosis, periodontitis, etc.).

In some implementations, the cleanse composition may increase user health and/or reduce inflammation (e.g., when administered with and/or without the renew composition).

One or more of the described compositions and/or processes may be administered in a residential setting. An individual may obtain the compositions and self-administer the compositions according to an administration process (e.g., schedule). Users satisfaction may be increased since the described compositions can be administered easily and in the privacy of a residential setting.

In some implementations, one or ore of the described compositions and/or processes may be administered in a commercial setting. For example, an individual may visit a spa, store, health facility, or other commercial establishment. When at the commercial setting, the individual may be diagnosed to obtain a proper administration schedule by another individual. The individual may stay at the commercial setting for administration of the compositions prescribed, in some implementations. The individual may then be able to ask questions during the cleanse and renew process, for example, from individuals at the commercial setting (e.g., health care professional, administrator, etc.) and/or the health of the individual may be monitored (e.g., for dehydration, for compliance with administration schedule, etc.). The commercial setting may also provide testing and/or be capable of analyzing test results to be utilized to develop diet recommendations and/or maintenance administration plans (e.g., composition and/or administration schedule recommendations).

EXAMPLES

Example 1

The cleanse composition may include approximately 1 ounce of magnesium sulfate heptahydrate (e.g., from Epsom salt) mixed with approximately 4 ounces to approximately 5 ounces of a mixture of juices and a sweetener. The mixture of juices may include blueberry and grape juices. The blueberry juice may be extracted from blueberries, and a blueberry remainder may remain after extraction. The cleanse composition may include at least 3/16 teaspoon of sweetener, such as stevia and/or sugar

Example 2

The renew composition may be a two part renew composition. The first part of the renew composition may include a first fiber component and a first set of probiotics. The first set of probiotics may include at least approximately 25 billion cultures of *Lactobacillus rhamnosus* GG. The second part of the renew composition may include a second fiber and a second set of probiotics. The second set of probiotics may include a plurality of strains of probiotics. The second set of probiotics may include at least approximately 25 billion cultures. The second set of probiotics may not include *Lactobacillus rhamnosus* GG.

The first fiber may include approximately 1 tablespoon to approximately 2 tablespoons of fiber component. The second fiber may include approximately 1 tablespoon to approximately 2 tablespoons of fiber component. The first fiber and the second fiber may include a fiber component from blueberries and/or apricots.

The fiber component from blueberries may be obtained from cold pressed processing of the blueberries, and drying and pulverizing the remainder from extraction to a powder. The blueberry remainder may include skins, pulp, and/or seeds. The blueberry remainder may be dried to a predetermined level of hydration (e.g., less than approximately 10%). The particle size of the blueberry remainder may be reduced before or after drying. For example, the dried blueberry remainder may be pulverized and utilized as the fiber component from blueberries in the first fiber and second fiber.

Example 3

The renew composition may include one or more probiotics. The intestinal maintenance composition may include a probiotic containing more than approximately 6 billion live organisms per administered dose.

Example 4

The intestinal maintenance composition may include one or more digestive enzymes such as Amylase 23,000 DU1, Protease 80,000 HUT1, Lipase 4,000 FIP1.

Example 5

In some implementations, a kit may be provided for improving and/or maintaining gastrointestinal health. The kit may include a cleanse composition of Example 1, a renew composition of Example 2, and an intestinal maintenance composition of Example 4.

The cleanse composition may be administered to an individual. The individual may be administered additional dosages after approximately 6 hours, if the cleanse is not complete (e.g., fluids exiting the body are not clear).

After the cleanse e.g., approximately 6 hours after the last dosage of cleanse composition administration), the renew compositions may be administered to the individual. The first set of probiotics and the second set of probiotics of the renew composition may be administered sequentially. The first set of probiotics may be administered and then the second set of probiotics may be administered at least 8 hours after administration of the first set of probiotics. For example, the first set of probiotics may be administered in the morning and the second set of probiotics may be administered in the evening. In some implementations, the second set of probiotics may be administered prior to the first set of probiotics. The sets of probiotics may be staggered to promote growth of both sets of probiotics in the intestinal tract.

In some implementations, the renew composition may be administered at least twice a day in the initial 24 hour period. The renew composition may be administered for more than 24 hours.

In some implementations, the intestinal maintenance composition may be administered prior to one or more meals. In some implementations, the intestinal maintenance composition may be administered prior to meals based on the composition of the meal. The intestinal maintenance period may last indefinitely until the time a follow-up cleanse cycle is repeated as chosen by a health practitioner or an individual's decision. The interval may be as short as one month, or as long as 1 year.

Example 6

In some implementations, the administration schedule of Example 5 may be followed for an individual. The renew composition of Example 3 may be administered for 1 week and then the renew composition of Example 4 may be administered (e.g., daily, twice daily, etc.) In place of the renew composition of Example 3. The replacement of the renew composition with a probiotic with lower number of cultures may reduce costs, and/or allow individuals to continue to promote healthy intestinal flora through the ingestion of probiotics.

In some implementations, daily fiber supplementation may not be well tolerated in individuals and replacement (e.g., after cleanse and/or after administration for a period of time of the renew composition of Example 3) of renew composition in Example 3 with the renew composition of Example 4 may allow administration of the probiotics without the daily fiber dosage.

Example 7

In some implementations, a kit may be provided for improving and/or maintaining gastrointestinal health. The kit may include a cleanse composition of Example 1, a renew composition of Example 3, and an intestinal maintenance composition of Example 4.

The cleanse composition may be administered to an individual. The individual ma be administered additional dosages after approximately 6 hours, if the cleanse is not complete (e.g., fluids exiting the body are not clear).

After the cleanse (e.g., approximately 6 hours after the last dosage of cleanse composition administration), the renew composition may be administered to the individual. In some implementations, the renew composition may be administered at least twice a day. The renew composition may be administered for 24 hours or more than 24 hours.

In some implementations, the intestinal maintenance composition may be administered prior to one or more meals.

Example 8

In some implementations, a kit may be provided for improving and/or maintaining gastrointestinal health. The kit may include a cleanse composition of Example 1, a renew composition of Example 2 or portion thereof, oral composition, and an intestinal maintenance composition of Example 4.

The cleanse composition may be administered to an individual. The individual may be administered additional dosages after approximately 6 hours, if the cleanse is not complete (e.g., fluids exiting the body are not clear).

After the cleanse (e.g., approximately 6 hours after the last dosage of cleanse composition administration), the renew compositions may be administered to the individual. At least one of the first set of intestinal probiotics (targeting the intestinal flora) and/or the second set of intestinal probiotics of the renew composition may be administered. An oral probiotic (targeting the oral flora) may be administered after the administration of the first set of probiotics and/or the second set of probiotics.

The first set of intestinal probiotics may be administered and then the oral probiotics may be administered at least 8 hours after administration of the first set of probiotics. For example, the first set of probiotics may be administered in the morning and the oral probiotics may be administered in the evening. In some implementations, the oral probiotics may be administered prior to the first set of probiotics. The sets of probiotics may be staggered to promote growth of both sets of probiotics in the intestinal tract.

In some implementations, the renew composition and the oral composition may each be administered at least once a day. The renew composition may be administered for 24 hours or more than 24 hours.

In some implementations, the intestinal maintenance composition may be administered prior to one or more meals. In some implementations, the intestinal maintenance composition may be administered prior to meals based on the composition of the meal.

Example 9

FIG. 1 illustrates an implementation of an example process 100 for improving intestinal health. An intestinal composition kit may be provided (operation 110). The intestinal kit may include a cleanse composition, renew composition(s), and/or intestinal maintenance composition.

One or more of the portions of the intestinal composition kit may be administered (operation 120). One or more of the administrations of intestinal compositions as described in Examples 5-8 may be followed for an individual.

An oral composition kit may be provided (process 130). The oral composition kit may include a dental powder, a toothpaste, a mouthwash, and/or oral probiotic composition. The dental powder may be granular (e.g., to whiten teeth) and may include calcium, magnesium, and *Streptococcus salivarius*. The toothpaste may include Bismuth subsalicylate. The mouthwash may include Bismuth subsalicylate. The oral probiotic composition may include any appropriate probiotics such as *Lactobacillus* species, *Bifidobacterium*, non-pathogenic Streptococci. The dental powder and/or toothpaste may be brushed into the teeth and gums and followed by rinsing with the mouthwash and/or water. Oral probiotic compositions may be provided after rinsing.

The oral composition kit may be administered (operation 140). Administration of one or more oral compositions may supplement the administration of the intestinal compositions. In some implementations, a dental powder, toothpaste, mouthwash, and/or oral probiotic composition may be administered daily (e.g., once a day, twice a day, etc.). For example, the dental powder, toothpaste, mouthwash, and/or oral probiotic may be administered in the morning, night, and/or after meals.

The promotion of healthy mouth flora via the administration of the oral compositions may promote healthy intestinal flora.

Example 10

Optionally, an individual may limit diet intake to fruits and/or vegetables approximately one day before administration of cleanse composition.

One dosage of the cleanse composition may be administered. The cleanse composition may include Magnesium sulfate. The cleanse composition may also include fruit juice such as blueberry juice, and/or green tea. The cleanse composition may be sweetened for example, by blueberry juice and/or a sweetener such as stevia. In some implementations, the individual may be quickly administered (e.g., in less than approximately 10 minutes) at least 8 ounces of water (e.g., at room temperature) and may be more slowly administered (e.g., in less than approximately 20 minutes) an additional at least 8 ounces of water.

After approximately 2 hours, approximately 1 to 2 cups of green tea (e.g., brewed green tea) may be administered at a temperature above room temperature. The warm beverage may improve cleanse results.

An additional dosage of the cleanse composition may be inhibited in the 3-5 hours after administration of the first dosage of the cleanse composition if the individual is experiencing intestinal clearing bowel activity. Additional juice may be administered to individuals experiencing intestinal bowel activity. An additional dosage of the cleanse composition may be administered after approximately 5 hours, if the individual is not experiencing intestinal clearing bowel activity. If the additional dosage of the cleanse composition is administered, the individual may be quickly administered (e.g., in less than approximately 10 minutes) at least 8 ounces of water (e.g., at room temperature) and may be more slowly administered (e.g., in less than approximately 20 minutes) an additional at least 8 ounces of water after the additional dosage of the cleanse composition.

Example 11

After the administration of the cleanse composition, such as according to Example 10, the renew composition may be administered. At least approximately 8 hours after the administration of the cleanse composition, a first renew composition that includes fiber and at least one high efficacy probiotic may be administered. The first renew composition may include approximately ¼-¾ teaspoons blueberry fiber. The fiber and the probiotic may be administered separately (e.g., via a solution and via a capsule, respectively).

Approximately 6-8 hours after administration of the first renew composition, a second renew composition may be administered. The second renew composition may include fiber and a second probiotic. The second renew composition may include approximately ¼-¾ teaspoons blueberry fiber. The second renew composition may include probiotics such as *Lactobacillus acidophilus, Lactobacillus plantarum, Lactobacillus rhamnosus, Bifidobacterium bifidus, Lactobacillus salivarius, Bificobacterium bifandus, Bifidobacterium lactis*, and/or *Bifidobacterium longum*. The fiber and the probiotic may be administered separately (e.g., via a solution and via a capsule, respectively).

The administration of the first and second renew compositions may be repeated (e.g., with at least 8 hours between administration) for a predetermined amount of time (e.g., 1 day, 2 days, 3 days, 1 week, daily, weekly, etc.).

In some implementations, diet of the individual may be restricted. For example, the individual may wait a predetermined period of time prior to resuming a regular and/or healthy diet. As another example, an individual may wait until the cleanse is approximately complete (e.g., passing out fairly clear brownish or dark fluid rather than stool) before introduction of solid fruits and vegetables.

End Of Examples

Various processes may be implemented by various systems or components thereof. In addition, various operations may be added, deleted, and/or modified in the described processes. In some implementations, described process(es) may be performed in combination with other processes or portions thereof.

U.S. patent application Ser. No. 15/096,489 entitled "Dental Hygiene Systems" is fully incorporated herein to the extent that it does not contradict with the described systems and processes.

Although users or individuals have been described as a human, a user may be a person or a group of people. For example, a first user may administer the oral and/or intestinal compositions to a second user. In some implementations, a first user may administer the oral and/or intestinal compositions to a second user that is a pet or other animal. For example, a first user (e.g., pet owner, veterinarian, pet groomer, etc.) may apply the oral and/or intestinal compositions, as described herein, to a dog's mouth or cat's mouth. Administering the oral and/or intestinal compositions to an animal may increase whiteness of teeth, inhibit cavities, improve gastrointestinal health and/or flora, and/or otherwise promote hygiene, in various implementations.

It is to be understood the implementations are not limited to particular systems or processes described which may, of course, vary. It is also to be understood that the terminology used herein is for the purpose of describing particular implementations only, and is not intended to be limiting. As used in this specification, the singular forms "a", "an" and "the" include plural referents unless the content clearly indicates otherwise. Thus, for example, reference to "a probiotic" includes a combination of two or more probiotic and reference to "a composition" includes different types and/or combinations of compositions.

Although the present disclosure has been described in detail, it should be understood that various changes, substitutions and alterations may be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A method of orally administering one or more compositions to improve or maintain gastrointestinal health of an individual, the method comprising:

orally administering one or more cleanse compositions, wherein at least one of the cleanse compositions comprises:

approximately 20 cc to approximately 40 cc of magnesium sulfate; and approximately 4 ounces to approximately 5 ounces of fruit juice, and wherein the fruit juice comprises blueberry juice;

wherein the one or more cleanse compositions cleanses a bowel of the individual in less than approximately 24 hours as determined by clear fluids leaving a gastrointestinal tract of the individual; and orally administering one or more renew compositions after administration of the one or more cleanse compositions, wherein at least one of the renew compositions comprises fiber and probiotic, wherein the probiotic comprises a first set of probiotics including a high efficacy strain and a second set of probiotics, wherein the first set of probiotics comprises a greater number of active cultures per dose than the second set of probiotics, wherein the second set of probiotics comprises from about 8 billion to about 10 billion active cultures of *Lactobacillus acidophilus, Lactobacillus plantarum, Lactobacillus rhamnosus, Lactobacillus salivarius, Bifidobacterium bifidum, Bifidobacterium lactis, Bifidobacterium longum*, or combinations thereof, wherein administration of the one or more renew compositions after the administration of the one or more cleanse compositions improves or maintains gastrointestinal health of the individual; and orally administering one or more maintenance compositions after administration of the one or more renew compositions, wherein at least one of the maintenance compositions comprises one or more vegetarian-sourced digestive enzymes selected from the group consisting of amylase, protease, lactase, lipase, cellulase, maltase, and hemicellulase.

2. The method of claim 1 wherein the one or more cleanse composition further comprises green tea.

3. The method of claim 1 wherein the one or more cleanse composition comprises approximately 20 to approximately 40 cc of powdered magnesium sulfate dissolved in the fruit juice.

4. The method of claim 1 wherein the fruit juice further comprises grape juice.

5. The method of claim 1 wherein the one or more cleanse composition further comprises approximately 3/16 to approximately 1/4 teaspoon of sweetener.

6. The method of claim 1 wherein the fiber of the one or more renew compositions comprises blueberry fiber, and wherein the blueberry fiber comprises remnants of blueberries after blueberry juicing.

7. The method of claim 1 further comprising:

orally administering the one or more maintenance compositions, wherein the one or more maintenance compositions further comprises fiber and probiotics, wherein the one or more maintenance compositions are not the same as the one or more renew compositions.

8. The method of claim 7 wherein the fiber in the maintenance composition comprises blueberry fiber.

9. The method of claim 1 wherein the at least one of the cleanse compositions comprises stevia.

10. The method of claim 1 wherein the cleanse composition cleanses a bowel in less than approximately 6 hours.

11. The method of claim 1 wherein the fiber of the renew composition comprises at least one fruit derived fiber.

12. The method of claim 1 wherein the fiber of the renew composition comprises at least one fruit derived fiber, and wherein the at least one fruit derived fiber comprises at least a portion of the skins, seeds, and pulps of fruit from which the at least one fruit derived fiber derives.

13. The method of claim 1, further comprising:

topically administering an oral probiotic composition to the mouth of an individual, wherein the oral probiotic composition comprises at least one first bacteria associated with oral health and at least one second bacteria associated with gastrointestinal health, and wherein the probiotic composition is administered via an immediate delivery vehicle; wherein administration of the probiotic compositions with the administration of the cleanse compositions improves or maintains lower gastrointestinal health of an individual.

14. The method of claim 13, wherein the at least one first bacteria associated with oral health comprises *Streptococcus salivarius* BLIS K12; and wherein the at least one second bacteria associated with gastrointestinal health in the oral probiotic composition comprises *Lactobacillus rhamnosus, Lactobacillus paracasei, Lactobacillus plantarum, Lactobacillus reuteri*, and *Lactobacillus salivarius.*

15. The method of claim 13, further comprising:

topically administering a dental powder to a mouth of an individual prior to administering the oral probiotic composition; administering a mouthwash to the mouth of the individual prior to administering the oral probiotic composition.

16. The method of claim 1, wherein at least a portion of the probiotic in the renew composition comprises a dormant probiotic that is revived by rehydration from fluids present in a gastrointestinal tract, fluids consumed with the renew composition, fluids in which the renew composition is mixed, or combinations thereof.

* * * * *